(12) United States Patent
Lang et al.

(10) Patent No.: US 8,197,816 B2
(45) Date of Patent: Jun. 12, 2012

(54) **HUMAN MONOCLONAL ANTIBODY SPECIFIC FOR LIPOPOLYSACCHARIDES (LPS) OF THE *PSEUDOMONAS AERUGINOSA* IATS O11 SEROTYPE**

(75) Inventors: Alois B. Lang, Helmberg (CH); Michael P. Horn, Thun (CH); Martin A. Imboden, Munsingen (CH); Adrian Zuercher, Bern (CH)

(73) Assignee: Kenta Biotech AG, Zurich, Schlieren (CH)

( * ) Notice: Subject to any disclaimer, the term of this patent is extended or adjusted under 35 U.S.C. 154(b) by 847 days.

(21) Appl. No.: 11/884,163

(22) PCT Filed: Feb. 13, 2006

(86) PCT No.: PCT/EP2006/001289
§ 371 (c)(1),
(2), (4) Date: Nov. 10, 2008

(87) PCT Pub. No.: WO2006/084758
PCT Pub. Date: Aug. 17, 2006

(65) Prior Publication Data
US 2009/0068191 A1  Mar. 12, 2009

(30) Foreign Application Priority Data

Feb. 14, 2005 (EP) .................... 05003095

(51) Int. Cl.
*A61K 39/40* (2006.01)
*A61K 39/395* (2006.01)
*A61K 39/00* (2006.01)

(52) U.S. Cl. ............... 424/150.1; 424/130.1; 424/133.1; 424/137.1; 424/141.1; 424/142.1; 424/164.1; 424/170.1; 424/178.1; 530/300; 530/350

(58) Field of Classification Search ............... 424/130.1, 424/133.1, 137.1, 141.1, 142.1, 150.1, 164.1, 424/170.1, 178.1; 530/300, 350
See application file for complete search history.

(56) References Cited

U.S. PATENT DOCUMENTS
5,627,067 A  5/1997 Siadak et al.

FOREIGN PATENT DOCUMENTS
WO  01/57226  8/2001
WO  02/20619  3/2002

OTHER PUBLICATIONS

Zweerink, et al., "Human Monoclonal Antibodies that Protect Mice against Challenge with *Pseudomonas aeruginosa*," *Infection and Immunity*, Aug. 1998, 56(8):1873-1879.
Collins, et al., "Opsonic and protective activity of five human IgM monoclonal antibodies reactive with lipopolysaccharide antigen of *Pseudomonas aeruginosa*," *FEMS Microbiology Immunology*, 1990, 64:262-268.
Akahori, et al., "Homo sapiens IGK mRNA for immunoglobin kappa light chain VLJ region, partial eds, clone:K61," 2001, Accession No. AB064102, http://www.ncbi.nlm.nih.gov/nuccore/AB06402.
Wang, et al., "Homo sapiens clone sc48u-20 immunoglobin heavy chain variable region (IgH) mRNA, partial eds," *Clin. Immunol.*, 1999, 93(2):132-142.
Altschul, et al., "Basic Local Alignment Search Tool," *J. Mol. Biol.*, 1990, 215:403-410.
Benetti, et al., "Expression and Characterization of the Recombinant Catalytic Subunit of Casein Kinase II from the Yeast *Yarrowia lipolytica* in *Escherichia coli*," *Protein Expression and Purification*, 1998, 13:286-290.
Bruderer, et al., "Affinities of endotoxin-specific human monoclonal antibodies, their polyclonal counterparts and murine monoclonal antibodies," *Res. Immunol.*, 1993, 144:659-665.
Persic, et al., "An integrated vector system for the eukaryotic expression of antibodies or their fragments after selection from phase display libraries," *Gene*, 1997, 187:9-18.
Cryz, et al., "Safety and Immunogenicity of a *Pseudomonas aeruginosa* O-Polysaccharide Toxin A Conjugate Vaccine in Humans," *J. Clin. Invest.*, 1987, 80:51-56.
Dean, et al., "The *wbpM* gene in *Pseudomonas aeruginosa* serogroup O17 resides on a cryptic copy of the serogroup O11 O antigen gene locus," *FEMS Microbiology Letters*, 2000, 187:59-63.
Devereux, et al., "A comprehensive set of sequence analysis programs for the VAX," *Nucleic Acids Research*, 1984, 12(1): 387-395.
Harrison, et al., "Pharmacokinetics, Tolerability, and Preliminary Efficacy of Human Anti-*Pseudomonas aeruginosa* Monoclonal Antibodies in Pneumonia and Burn Infection Patients," *Hybridoma*, Nov. 1997, 16:413-420.
Henikoff, et al., "Amino acid substitution matrices from protein blocks," *Proc. Natl. Acad. Sci. USA*, Nov. 1992, 89:10915-10919.
Lang, et al., "Prophylaxis and therapy of *Pseudomonas aeruginosa* infection in cystic fibrosis and immunocompromised patients," *Vaccine*, 2004, 22S:S44-S48.
Needleman, et al., "A General Method Applicable to the Search for Similarities in the Amino Acid Sequence of Two Proteins," *J. Mol. Biol.*, 1970, 48:443-453.
Rudikoff, et al., "Single amino acid substitution altering antigen-binding specificity," *Proc. Natl. Acad. Sci. USA*, Mar. 1986, 79:1979-1983.
Tamura, et al., "Structural Correlates of an Anticarcinoma Antibody: Identification of Specificity-Determining Residues (SDRs) and Development of a Minimally Immunogenic Antibody Variant by Retention of SDRs Only," *The Journal of Immunology*, 2000, 164:1432-1441.
"Infection" (2012). In *The Free Online Medical Dictionary* (© 2012 Farlex, Inc.). Retrieved from http://www.medical-dictionary. thefreedictionary.com/infection (retrieved on Feb. 20, 2012).

*Primary Examiner* — Rodney P. Swartz
(74) *Attorney, Agent, or Firm* — Riverside Law LLP

(57) ABSTRACT

The present invention relates to a human monoclonal antibody specific for the serotype IATS O11 of *P. aeruginosa*, a hybridoma producing it, nucleic acids encoding it, and host cells transfected therewith. Further, the present invention relates to methods for producing said monoclonal antibody. In addition, the present invention relates to pharmaceutical compositions comprising at least one antibody or at least one nucleic acid encoding said antibody.

14 Claims, 7 Drawing Sheets

Figure 1

```
¹GAGGAGCAGGTGGTGGAGTCCGGGGGAGGCTTTGTTCAGCCTGGGGGGTCCCTGAGACTC      60
  E  E  Q  V  V  E  S  G  G  G  F  V  Q  P  G  G  S  L  R  L      20

TCCTGTGCAGCCTCTGGATTCACCTTTAGTCCATACTGGATGCACTGGGTCCGCCAAGCT    120
  S  C  A  A  S  G  F  T  F  S  P  Y  W  M  H  W  V  R  Q  A      40
                               CDR1

CCAGGGAAGGGGCTGGTGTGGGTCTCACGTATTAATAGTGATGGGAGCACATACTACGCG    180
  P  G  K  G  L  V  W  V  S  R  I  N  S  D  G  S  T  Y  Y  A      60
                              CDR2

GACTCCGTGAAGGGCCGATTCACCATCTCCAGAGACAACGCCAGGAACACACTGTATCTG    240
  D  S  V  K  G  R  F  T  I  S  R  D  N  A  R  N  T  L  Y  L      80

CAAATGAACAGTCTGAGAGCCGAGGACACGGCTGTGTATTACTGTGCAAGAGATCGATAC    300
  Q  M  N  S  L  R  A  E  D  T  A  V  Y  Y  C  A  R  D  R  Y     100
                                                    CDR3

TATGGCCCCGAAATGTGGGGCCAAGGGACAATGGTCACCGTCTCTTCA                348
  Y  G  P  E  M  W  G  Q  G  T  M  V  T  V  S  S                 116
```

Figure 2

```
¹GATGTTGTGATGACTCAGTCTCCGCTCTCCCTGCCCGTCACCCTTGGACAGCCGGCCTCC    60
  D  V  V  M  T  Q  S  P  L  S  L  P  V  T  L  G  Q  P  A  S    20

ATCTCCTGCAGGTCTAGTCAAAGCCTCGTATATAGTGATGGAAACACCTACTTGAATTGG   120
 I  S  C  R  S  S  Q  S  L  V  Y  S  D  G  N  T  Y  L  N  W    40
            ─────────────────CDR1──────────────────

TTTCAGCAGAGGCCAGGCCAATCTCCAAGGCGCCTAATTTATAAGGTTTCTAACCGGGAC   180
 F  Q  Q  R  P  G  Q  S  P  R  R  L  I  Y  K  V  S  N  R  D    60
                                      ────────CDR2──────

TCTGGGGTCCCAGACAGATTCAGCGGCAGTGGGTCAGGCACTGATTTCACACTGAAAATC   240
 S  G  V  P  D  R  F  S  G  S  G  S  G  T  D  F  T  L  K  I    80
 ─

AGCAGGGTGGAGGCTGAGGATGTTGGGGTTTATTACTGCATGCAAGGTACACACTGGCCT   300
 S  R  V  E  A  E  D  V  G  V  Y  Y  C  M  Q  G  T  H  W  P   100
                                      ────────CDR3──────

CTCACTTTCGGCGGAGGGACCAAGGTGGAGATCAAA                           336
 L  T  F  G  G  G  T  K  V  E  I  K                            112
```

HUMAN MONOCLONAL ANTIBODY SPECIFIC FOR LIPOPOLYSACCHARIDES (LPS) OF THE *PSEUDOMONAS AERUGINOSA* IATS O11 SEROTYPE

CROSS-REFERENCE TO RELATED APPLICATIONS

This application is the U.S. national phase application filed under 35 U.S.C. §371 claiming benefit to International Patent Application No. PCT/EP2006/001289, filed on Feb. 13, 2006, which is entitled to priority under 35 U.S.C. §119(a) and §365(b), to European Application No. 05003093.6, filed Feb. 14, 2005, each of which application is hereby incorporated herein by reference in its entirety.

The present invention relates to a human monoclonal antibody specific for the serotype IATS O11 of *P. aeruginosa*, a hybridoma producing it, nucleic acids encoding it, and host cells transfected therewith. Further, the present invention relates to methods for producing said monoclonal antibody, In addition, the present invention relates to pharmaceutical compositions comprising at least one antibody or at least one nucleic acid encoding said antibody.

*P. aeruginosa* is a ubiquitous gram-negative environmental bacterium found in flesh water and soil. It is a classical opportunistic pathogen that does not normally pose a threat to the immunocompetent host, who clears it by means of opsonizing antibodies and phagocytosis. However, cystic fibrosis patients and immunocompromised individuals—including burn victims, intubated patients in ICU, cancer and AIDS patients, as well as patients undergoing organ transplantation—are at particularly high risk of contracting nosocomial infections. Together with methicillin-resistant *S. aureus* (MRSA) and vancomycin-resistant *enterococci* (VRE), *P. aeruginosa* is responsible for up to 34% of all nosocomial infections which have increased from 7.2/1000 patient days in 1975 to 9.8/1000 patient days in 1995. Among the most frequently observed forms of nosocomial infection are bloodstream infections and pneumonia.

For the prevention of chronic *P. aeruginosa* infections in cystic fibrosis patients, an octavalent conjugate-vaccine consisting of the 8 most relevant LPS serotypes of *P. aeruginosa* coupled to detoxified Toxin A of *P. aeruginosa* has been established for active immunization. Long-term studies with this vaccine have shown that the ratio of chronically infected patients dropped from about 72% to 32% at the age of 18 years. However, active vaccination is only possible in immunocompetent patients, as well as in predictable situations. Thus, most of the *P. aeruginosa* victims cannot be immunized actively with the octavalent vaccine. Due to this and due to the fact that most *P. aeruginosa* strains are multi-drug resistant, there is a need for an alternative therapeutic tool to treat *P. aeruginosa*-infected patients. One attempt is to create human monoclonal anti-bodies by means of classical hybridoma technology or phage display repertoire cloning.

Both methods and the antibodies created thereby show serious drawbacks.

The classical hybridoma technology ("Kohler and Milstein" approach) is based on eliciting murine B cells of desired specificity by active immunization with an antigen of choice and immortalization by fusion with a myeloma partner. Thereafter, the genetic information of an antibody-producing clone needs to be humanized by genetic engineering, and the antibody to be produced in a suitable expression system. Likewise, phage display repertoire cloning requires a sophisticated genetic engineering of the antibody and establishment of a suitable expression system.

It is known that murine monoclonal antibodies directed to bacterial LPS recognize other epitopes than human antibodies. Therefore, generation of monoclonal antibodies in mice followed by humanization would not necessarily result in the isolation of antibodies with specificity relevant for the use in humans.

Furthermore, antibodies of IgM isotype are most effective due to effector mechanisms linked to IgM that are optimal for antibacterial immunity. However, to date recombinant expression of IgM antibodies has not been achieved because of the complex, pentameric form of this molecule. Consequently, expression of antibodies isolated by phage-display technology is limited to isotypes other than IgM.

Alternatively, there have been different attempts in generating human monoclonal anti-bodies to LPS moieties of *P. aeruginosa*. However, either the methods used for producing said antibodies were disadvantageous (due to the instability of lymphoblastoid cells), or the antibodies exhibited a non-human glycosylation pattern, or very large quantities of the antibody were required. Moreover, many of the antibodies described in the prior art lack effector functions and thus were not protective.

Accordingly, one technical problem underlying the present invention is to provide a human monoclonal antibody specific to LPS of a particular serotype of *P. aeruginosa* wherein the antibody exhibits high protective capacity, in particular in vivo.

The technical problem is solved by the human monoclonal antibodies as defined in the following.

According to the present invention, a human monoclonal antibody termed 1BO11, specific for LPS of the *P. aeruginosa* serotype IATS O11 is provided wherein the variable region of the light chain of the antibody comprises at least one of SEQ ID NO:1 in the CDR1 region, SEQ ID NO: 2 in the CDR2 region and SEQ ID NO:3 in the CDR3 region, and wherein the variable region of the heavy chain of the antibody comprises at least one of SEQ ID NO:4 in the CDR1 region, SEQ ID NO:5 in the CDR2 region and SEQ ID:NO. 6 in the CDR3 region; or a fragment or derivative thereof capable of binding to said LPS.

The present invention further provides a hybridoma capable of producing the monoclonal antibody and nucleic acids encoding the light and heavy chain of the antibody, respectively. Further, the present invention provides vectors and host cells, comprising the nucleic acid. In addition, methods for producing the monoclonal antibodies are provided. In addition, pharmaceutical compositions comprising at least one antibody and/or at least one nucleic acid and second medical uses thereof are provided.

Surprisingly, it has been found that the human monoclonal antibodies according to the invention exhibit high protective capacity. In particular, the human monoclonal antibody proved to be opsonophagocytic in vitro. Even more important, the monoclonal antibodies according to the present invention exhibit in vivo protective capacity as determined by the protection from blood-stream infection in the murine burn wound model as well as the protection from respiratory tract infection in an acute lung infection model in mice as shown in the examples.

With the human monoclonal antibodies according to the invention, opsonophagocytosis at much lower doses as well as a higher protection is achieved compared to the human monoclonal antibodies described by Collins et al. (Collins M S et al., 1990. FEMSIM 64:263-268).

In contrast to the monoclonal antibodies described in the state of the art (Harrison F J J et al. 1997. Hybridoma 16(5): 413-420; Zweerink H J et al. 1988. Infection and Immunity 56(8):1873-1879), the human monoclonal antibodies according to the invention are further generated from blood of a healthy individual actively immunized with a conjugate vaccine. It is generally known that antibodies against polysaccharides are of minor quality (i.e. low-affinity with little effector potential) because of the lack of T-cell help. Only through the use of a conjugate vaccine valuable antibodies having high affinity with strong effector potential against polysaccharide targets can be generated. More-over, the production rate of the human monoclonal antibodies according to the invention is higher compared to the production rate of monoclonal antibodies described in the state of the art (Zweerink H J et al. 1988. Infection and Immunity 56(8):1873-1879).

No human monoclonal antibody is described in the state of the art showing protection from lung infection caused by *P. aeruginosa*.

According to the present invention, the antibody is specific for the LPS of *P. aeruginosa* serotype IATS O11 and exhibits opsonophagocytic activity at concentrations as low as 0.1 ng/ml as determined using fluorescence-conjugate bacteria. No prior art antibody has been reported exhibiting an opsonophagocytic activity at this low dosage.

The monoclonal antibody according to the present invention recognizes clinical isolates with high specificity. 18 of 20 samples of patients infected with *P. aeruginosa* of the IATS O11 serotype were identified using this antibody. Without being bound by theory, it is assumed that the monoclonal antibody is capable of recognizing all *P. aeruginosa* strains of IATS O11 known in the prior art. This property renders the antibody particularly useful for diagnosis and therapy. Thus, the antibody according to the present invention exhibits an insurmountable reliability.

The term "human monoclonal antibody" as used herein encompasses any partially or fully human monoclonal antibody independent of the source from which the monoclonal antibody is obtained. The production of the human monoclonal antibody by a hybridoma is preferred. The monoclonal antibody may also be obtained by genetic engineering and in particular CDR grafting of the CDR segments as defined in the claims onto available monoclonal antibodies by replacing the CDR regions of the background anti-body with the specific CDR segments as defined in the claims.

The term "CDR region" means the complementarity determining region of an antibody, i.e. the region determining the specificity of an antibody for a particular antigen. Three CDR regions (CDR1 to CDR3) on both the light and heavy chain are responsible for antigen binding.

The positions of the CDR regions within the heavy chain are as follows:
CDR1 region amino acids 31 to 35 within the $V_H$ exon,
CDR2 region amino acids 50 to 65 within the $V_H$ exon,
CDR3 region amino acids 95 and following amino acids within the $V_H$ exon.

The positions of the CDR regions are independent from the class of antibody, i.e. IgM, IgA of IgG.

The positions of the CDR regions of the kappa light chain are as follows:
CDR1 region amino acids 24 to 34 within the $V_\chi$ exon,
CDR2 region amino acids 50 to 56 within the $V_\chi$ exon,
CDR3 region amino acids 89 and following amino acids within the $V_\chi$ exon.

The positions of the CDR region within the lambda type light chain are as follows:
CDR1 region amino acids 24 to 34 within the $V_\lambda$ exon,
CDR2 region amino acids 50 to 56 within the $V_\lambda$ exon,
CDR3 region amino acids 89 and following amino acids within the $V_\lambda$ exon.

Amino acid alignments of the $V_H$, $V_\chi$ and $V_\lambda$, exon can be obtained from V base index. (http://www dot mrc-cpe dot cam dot ac dot uklvbase-ok dot php?menu=901).

The term "serotype" means any known serotype of *P. aeruginosa*. A concordance table of the different nomenclatures presently used for different *P. aeruginosa* serotypes is shown in table I in the specification.

The term "fragment" means any fragment of the antibody capable of binding to the LPS serotype. The fragment has a length of at least 10, preferably 20, more preferably 50 amino acids. It is preferred that the fragment comprises the binding region of the antibody. It is preferred that the fragment is a Fab or F(ab')$_2$ fragment or a mixture thereof.

The term "derivative" encompasses any muteins of the human monoclonal antibody differing by the addition, deletion, and/or substitution of at least one amino acid. Preferably, the derivative is a mutein of the human monoclonal antibody wherein the mutein carries at least one conservative substitution in any of the CDR's in the heavy chain and/or light chain as indicated in the claims. More preferably, the mutein has not more than 5, particularly preferred not more than 2 conservative substitutions. The capacity of the fragment or derivative of the antibody to bind to the particular LPS serotype is determined by direct ELISA as described in the material and methods section: the particular LPS is immobilized on the solid phase of ELISA plates. Antibody fragments or derivative of the antibodies are incubated with the immobilized LPS, and bound anti-bodies or derivatives thereof are visualized by a suitable enzyme-conjugated secondary antibody.

In accordance with the present invention, the term "conservative substitution" means a replacement of one amino acid belonging to a particular physico-chemical group with an amino acid belonging to the same physico-chemical group. The physico-chemical groups are defined as follows:

The group of non-polar amino acids comprises: glycine, alanine, valine, leucine, isoleucine, methionine, proline, phenylalanine, and tryptophan. The group of amino acids having uncharged polar side chains comprises asparagine, glutamine, tyrosine, cysteine, and cystine. The physico-chemical group of amino acids having a positively charged polar side chain comprises lysine, arginine, and histidine. The physico-chemical group of amino acids having a negatively charged polar side chain comprises aspartic acid and glutamic acid, also referred to as aspartate and glutamate.

According to the present invention, an antibody specific for LPS of the *P. aeruginosa* serotype IATS O11 is provided as outlined above.

According to a further embodiment the present invention provides a human monoclonal antibody specific for LPS or the *P. aeruginosa* LPS serotype IATS O11 wherein the variable region of the light chain of the antibody has the amino acid sequence of SEQ ID NO:7 and the variable region of the heavy chain has the amino acid sequence of SEQ ID NO:8; or a variant of said antibody capable of binding said LPS wherein the variable region of the amino acid sequence of the light chain of the antibody is at least 85% homologous to SEQ ID NO:7 and the amino acid sequence of the variable region of the heavy chain of the antibody is at least 85% homologous to SEQ ID NO:8.

The term "homology" known to the person skilled in the art designates the degree of relatedness between two or more polypeptide molecules, which is determined by the agreement between the sequences. The percentage "homology" is found from the percentage of homologous regions in two or more sequences, taking account of gaps or other sequence features.

The homology of mutually related polypeptides can be determined by means of known procedures. As a rule, special computer programs with algorithms taking account of the special requirements are used. Preferred procedures for the determination of homology firstly generate the greatest agreement between the sequences studied. Computer programs for the determination of the homology between two sequences include, but are not limited to, the GCG program package, including GAP (Devereux J et al., Nucleic Acids Research 12 (12): 387 (1984); Genetics Computer Group University of Wisconsin, Madison (WI); BLASTP, BLASTN and FASTA (Altschul S et al., J. Molec. Biol. 215: 403-410 (1990)). The BLAST X program can be obtained from the National Centre for Biotechnology Information (NCBI) and from other sources (BLAST Handbook, Altschul S et al., NCB NLM NIH Bethesda Md. 20894; Altschul S et al., J. Mol. 215: 403-410 (1990)). The well-known Smith Waterman algorithm can also be used for the determination of homology.

Preferred parameters for the sequence comparison include the following:
Algorithm: Needleman and Wunsch, J. Mol. Biol. 48 (1970), 443-453
Comparison matrix: BLOSUM62 from Henikoff & Henikoff, PNAS USA 89 (1992), 10915-10919
Gap penalty: 12
Gap-length penalty: 2

The GAP program is also suitable for use with the above parameters. The above parameters are the standard parameters (default parameters) for amino acid sequence comparisons, in which gaps at the ends do not decrease the homology value. With very small sequences compared to the reference sequence, it can further be necessary to increase the expectancy value to up to 100,000 and in some cases to reduce the word length (word size) to down to 2.

Further model algorithms, gap opening penalties, gap extension penalties and comparison matrices including those named in the Program Handbook, Wisconsin Package, Version 9, September 1997, can be used. The choice will depend on the comparison to be performed and further on whether the comparison is performed between sequence pairs, where GAP or Best Fit are preferred, or between one sequence and a large sequence database, where FASTA or BLAST are preferred.

An agreement of 85% determined with the aforesaid algorithms is described as 85% homology. The same applies for higher degrees of homology.

In preferred embodiments, the muteins according to the invention have a homology of 85% or more, e.g. more than 90% or 95%.

It is further preferred that the light chain of the human monoclonal antibody according to the present invention is of the kappa or lambda type. Particularly preferred, the light chain is of the kappa type. The light chain may be either a naturally occurring chain including a naturally rearranged, a genetically modified or synthetic type of light chain. If the antibody according to the present invention being specific to IATS O11 is of the kappa type, then it is preferred that the light chain be derived from germ line DPK18 (http://www dot mrc-cpe dot cam dot ac dot uklALIGNMENTS dot php?menu=901#VKEX).

According to a further preferred embodiment, the heavy chain of the human monoclonal antibody of the present invention is selected from all human isotypes, namely IgM, IgA, or IgG. Preferably, the heavy chain is of the IgM type. If the antibody is of the IgM type, then it exhibits the advantageous properties of high avidity for *P. aeruginosa* LPS, effectively binds complement and thus mediates either direct killing of bacteria, and/or efficiently opsonizes bacteria for phagocytosis. Further, IgM is resistant to the proteolytic degradation by *P. aeruginosa* elastase, whereas other isotypes like IgG or IgA can be degraded. IgM antibodies are effective in low amounts. 1 to 4 µg per mouse were fully protective in the murine burn wound sepsis model.

It is preferred that the variable heavy chain be derived from germ line DP-53 (http://www dot mrc-cpe dot cam dot ac dot uklALIGNMENTS dot php?menu=901#VKEX). The light chain and heavy chain may either be covalently linked as a single-chain antibody (e.g. bivalent scFv, bifunctional scFv and bispecific scFv) or non-covalently linked with each other.

According to a preferred embodiment of the present invention, the human monoclonal antibody consists entirely of human amino acid sequence.

"Consists entirely of human amino acid sequence" means that the amino acid sequence of the human monoclonal antibody is derived from a human germ line. This may be obtained in different ways. For example, the human monoclonal antibody consisting of human amino acid sequence can be obtained from a hybridoma wherein the B-cell is a human B-cell. Alternatively, the human monoclonal antibody may be obtained by CDR grafting of the CDR regions as indicated in the claims onto available human monoclonal antibodies thereby producing a human monoclonal antibody specific for a *P. aeruginosa* LPS serotype in accordance with the present invention.

The entirely human amino acid sequence of the human monoclonal antibody prevents the occurrence of undesired adverse effects such as rejection reactions or anaphylactic shock.

Further preferred, the human monoclonal antibody exhibits essentially human antigen recognition. "Essentially human antigen recognition" means that the antigen recognition by the human monoclonal antibody according to the present invention is essentially identical to the recognition of antigen by a human healthy individual. In particular, it is required that the Fc portions of the light and heavy chain of the human monoclonal antibody are of human type in order to ensure interaction with the human immune system, and to reduce the risk of generation of so called HAMA (human anti-mouse antibodies).

According to a further preferred embodiment, the human monoclonal antibody of the present invention is obtainable from a human B-cell or a hybridoma obtained by fusion of said human B-cell with a myeloma or heteromyeloma cell.

Human B-cells may be obtained by immunization of healthy individuals or patients and subsequent removal of blood samples from which human B-cells can be isolated in a known manner (Current Protocols in Immunology. Chapter 7.1. Isolation of whole mononuclear cells from peripheral blood and cord blood. Published by Wiley & sons, Eds: J C Coligan et al.). The human B-cell may be fused to a myeloma or heteromyeloma to produce a hybridoma in accordance with known techniques according to the classical Kohler and Milstein approach. Suitable myeloma cells are derivatives of P3X63 such as P3X63Ag8.653 (ATCC CRL-1580) or SP2/0 (ATCC CRL-1646). Suitable heteromyeloma cells are e.g. F3B6 (ATCC HB-8785). The resulting hybridoma may be selected according to known procedures. The hybridomas are cultured in a suitable culture medium and the produced antibody is recovered from the supernatant.

Further, the present invention provides nucleic acids encoding the heavy chain and light chain, respectively, of the human monoclonal antibody of the present invention. The nucleic acid may be a naturally occurring nucleic acid either derived from the germ line or from rearrangement occurring in B-cells, alternatively the nucleic acids may be synthetic. Synthetic nucleic acids also include nucleic acids having modified internucleoside bonds including phosphothioester to increase resistance of the nucleic acids from degradation. The nucleic acid may be genetically engineered or completely synthetically produced by nucleotide synthesis.

The present invention further provides vectors comprising at least one nucleic acid encoding the light chain of the human monoclonal antibody of the present invention and/or at least one nucleic acid encoding the heavy chain of the human monoclonal antibody of the present invention. The nucleic acids may be either present in the same vector or may be present in the form of binary vectors. The vector preferably comprises the promoter operatively linked to the nucleic acid in order to facilitate expression of the nucleic acid encoding the light and/or heavy chain. Preferably, the vector also includes an origin for replication and maintenance in a host cell. The vector may also comprise a nucleotide sequence encoding a signal sequence located 5' of the nucleic acid encoding the light chain or heavy chain. The signal sequence may facilitate secretion of the encoded chain into the medium.

Preferably, the vector is derived from adenoviruses, vaccinia viruses, baculoviruses, SV 40 viruses, retroviruses, plant viruses or bacteriophages such as lambda derivatives or M13. The particularly preferred vector is a vector containing the constant regions of human Ig heavy chains and human light chains, such as the integrated vector system for eukaryotic expression of immunoglobulins described by Persic et al (Persic et al. 1997. Gene. 187(1): 9-18).

The vector may further comprise a His-tag coding nucleotide sequence resulting in the expression of a construct for producing a fusion product with a His-tag at the N-terminus of the light and/or heavy chain of the human monoclonal antibody which facilitates purification of the protein at a nickel column by chelat formation.

Further, the present invention provides host cells comprising the vector and/or the nucleic acid suitable for the expression of the vector. In the art numerous prokaryotic and eukaryotic expression systems are known wherein eukaryotic host cells such as yeast cells, insect cells, plant cells and mammalian cells, such as HEK293-cells, PerC6-cells, CHO-cells, COS-cells or HELA-cells and derivatives thereof are preferred. Particularly preferred are human production cell lines. It is preferred that the transfected host cells secrete the produced antibody into the culture medium. If intracellular expression is achieved, then renaturation is performed in accordance with standard procedures such as e.g. Benetti P H et al., Protein Expr Purif Aug; 13:283-290, (1998).

The present invention also provides methods for producing the human monoclonal antibody. In one embodiment, the human monoclonal antibody is produced by culturing the above-described hybridoma. The produced monoclonal antibody is secreted into the supernatant and can be purified from it by applying conventional chromatographic techniques.

Alternatively, the human monoclonal antibody is produced by the host cell comprising a vector according to the present invention and culturing the host cell under conditions suitable for recombinant expression of the encoded antibody chain. Preferably, the host cell comprises at least one nucleic acid encoding the light chain and at least one nucleic acid encoding the heavy chain and is capable of assembling the human monoclonal antibody such that a 3-dimensional structure is generated which is equivalent to the 3-dimensional structure of a human monoclonal antibody produced by a human B-cell. If the light chain is produced separately from the heavy chain, then both chains may be purified and subsequently be assembled to produce a human monoclonal antibody having essentially the 3-dimensional structure of a human monoclonal antibody as produced by a human B-cell.

The human monoclonal antibody may also be obtained by recombinant expression of the encoded light and/or heavy chain wherein the nucleic acid is produced by isolating a nucleic acid encoding a human monoclonal antibody in a known manner and grafting of the nucleic acid sequence encoding the CDR's as defined in the claims onto the isolated nucleic acid.

According to a further preferred embodiment, the human monoclonal antibody according to the present invention is modified. The modifications include the di-, oligo-, or polymerization of the monomeric form e.g. by cross-linking using dicyclohexylcarbodiimide. The thus produced di-, oligo-, or polymers can be separated from each other by gel filtration. Further modifications include side chain modifications, e.g. modifications of $\epsilon$-amino-lysine residues, or amino and carboxy-terminal modifications, respectively. Further modifications include post-translational modifications, e.g. glycosylation and/or partial or complete deglycosylation of the protein, and disufide bond formation. The anti-body may also be conjugated to a label, such as an enzymatic, fluorescent or radioactive label.

The present invention further provides pharmaceutical compositions comprising at least one human monoclonal antibody and/or at least one nucleic acid encoding a light and/or heavy chain of the human monoclonal antibody.

The pharmaceutical composition may further comprise pharmaceutically acceptable ingredients known in the art.

Preferably, the pharmaceutical compositions are applied for the treatment of diseases caused by *P. aeruginosa* in infections such as blood-stream infection, pneumonia, chronic bronchitis, local infections including wound infections and invasive infections of joints, mainly in immunocompromised patients and/or in patients with compromised respiratory function. The pharmaceutical compositions are further intended for but not limited to the prophylaxis and/or treatment of hospital-acquired (nosocomial) infections. Since the main victims of *P. aeruginosa* infections are cystic fibrosis patients, burn victims, intubated patients, patients in surgical and/or medical intensive care units, cancer and AIDS patients, immunocompromised patients, immunosuppressed patients, diabetic patients, as well as intravenous drug abusers, the pharmaceutical compositions are in particular intended for prophylaxis and/or treatment of diseases caused by *P. aeruginosa* in said group of patients.

The pharmaceutical composition may further comprise antibiotic drugs, preferably coupled to the new monoclonal antibody.

The pharmaceutical compositions comprise the new monoclonal antibody in a concentration range of 0.1-30 mg/kg body weight.

The pharmaceutical compositions may be administered in any known manner such as intravenous, intramuscular, intradermal, subcutaneous, intra-peritoneal, topical, intranasal administration, or as inhalation spray.

The present invention also provides a test kit for the diagnosis of *P. aeruginosa* infections comprising at least one human monoclonal antibody of the present invention and optionally further suitable ingredients for carrying out a diagnostic test.

The test kit is suitable for the specific reliable diagnosis of a *P. aeruginosa* infection. A test assay may be based on a conventional ELISA test in liquid or membrane-bound form. The detection may be direct or indirect as known in the art wherein the antibody is optionally conjugated to an enzymatic, fluorescent or radioactive label.

The following examples illustrate the invention but are not intended to limit the scope of the present invention. Further embodiments will be apparent for the person skilled in the art when studying the specification and having regard to common general knowledge.

BRIEF DESCRIPTION OF THE FIGURES

FIG. 1 relates to DNA (SEQ ID NO:10) and amino acid sequence (SEQ ID NO:8) of 1BO11 heavy chain variable region.

FIG. 2 relates to DNA (SEQ ID NO:9) and amino acid sequence (SEQ ID NO:7) of 1BO11 kappa light chain variable region.

MATERIAL AND METHODS

Figure 3:
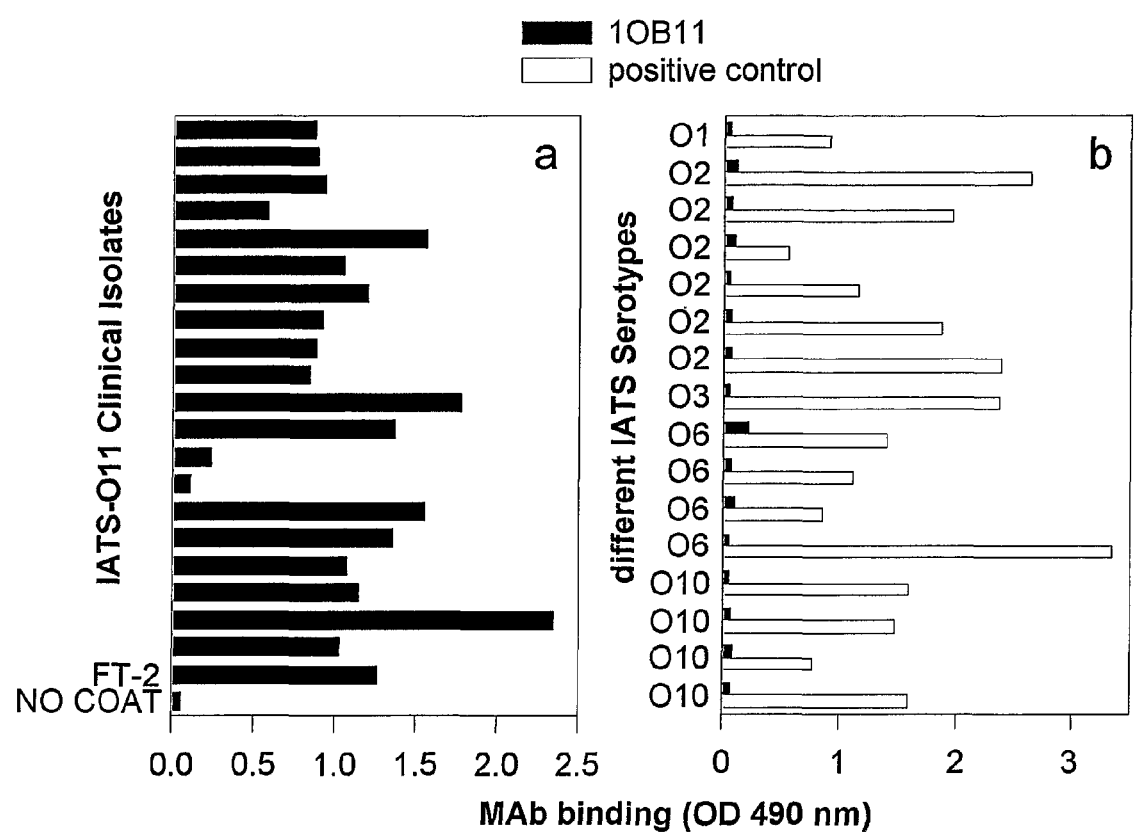
FIG. 3a relates to the recognition pattern of clinical *P. aeruginosa* isolates of the sero-type IATS O11 by the monoclonal antibody 1BO11.
FIG. 3b relates to the recognition pattern of clinical *P. aeruginosa* isolates of other serotypes by the monoclonal antibody 1BO11 in comparison with monoclonal antibodies specific for said other serotypes. The binding to 1BO11 was determined by whole cell ELISA.

The following Material and Methods have been used in the Examples:

Determination of LPS-Specificity and Quantification of IgM in Cell Supernatant

For screening and analysis of antibodies in cell culture supernatants, an ELISA was performed as described elsewhere (Cryz, S. J. et al., 1987. J. Clin. Invest. 80(1):51-56) with some alterations. Briefly, *P. aeruginosa* lipopolysaccharide (produced in house) LPS stock solutions were prepared at a concentration of 2 mg/ml in 36 mM triethylamine. For coating, the solution was diluted to 10 μg/ml in PBS containing 0.02% sodium azide (PBS-Az). This solution was mixed with an equal volume of 10 μg/ml methylated human serum albumine (HSA; produced in house as follows: 2 g of lyophilized HSA was dissolved in 200 ml absolute methanol. After adding 1.68 ml of 37% HCl, the solution is stored for at least 3 day at room temperature in the dark with occasional shaking. The precipitate is collected by a 10 min centrifugation (4500 rpm, GS1 rotor), and washed twice with absolute methanol and twice with anhydrous ether by suspending the pellet in the solvent. The precipitate is dried during 2 hours in a desiccator and the dry pellet is suspended in $H_2O$, and stored in aliquots at −20° C. Protein concentration was 8.05 mg/ml) in PBS-Az by gently stirring for 5 minutes at room temperature. NUNC® ELISA plates were coated with 100 μl/well LPS-HSA solution over night at room temperature. After washing the plates 3× with 300 μl PBS pH 7.4 (produced in house) containing 0.05% Tween20 (#93773; Fluka Chemie AG, Switzerland) (PBS-T), cell culture supernatants were incubated 1:2 diluted in PBS for 2 hours at 37° C. After washing the plates 3× with PBS-T, bound antibodies were detected with horseradish peroxidase-conjugated goat anti-human IgM antibody (#074-1003; KPL; Kirkegaard & Perry Laboratories, Inc. Gaithersburg, Md.) diluted 1:2000 in PBS containing 5% (v/v) FCS. The plates were incubated for 1 hour at 37° C., and washed 3× with PBS-T. Antibody-binding was visualized by adding 100 μl/well OPD (0.4 mg/ml Orthophenyldiamin in 24 mM citric acid and 52 mM di-sodium hydrogen phosphate containing 0.0012% (V/V) $H_2O_2$ substrate solution. Color reaction was stopped after 2-3 min by the addition of 50 μl/well 1 M HCl. Optical density was read on a ELISA reader at 490 nm using Softmax Pro® software.

For quantification of IgM in the cell culture supernatants, ELISA plates were coated with 1 μg/ml unconjugated goat anti-human IgM antibody in PBS over night at 4° C. Plates were washed 3× with PBS-T, and cell supernatants and standards were incubated in 2-fold dilutions. As standard human standard serum (Behring) was used starting at a concentration of 0.5 μg/ml. All dilutions were done in PBS-T. Plates were incubated for 2 hours at room temperature on a rocking table. After washing the plates 3× with PBS-T, bound antibodies were detected with horseradish peroxidase-conjugated goat anti-human IgM antibody (KPL) diluted 1:2000 in PBS containing 5% (v/v) FCS. The plates were incubated for 1 hour at room temperature on a rocking table, and washed 3× with PBS-T. Antibody-binding was visualized by adding 150 μl/well OPD substrate solution. Color reaction was stopped after 1 min by the addition of 50 μl/well 1 M HCl. Optical density was read on a ELISA reader at 490 nm using Softmax Pro® software.

Sequence Analysis

RNA of hybridoma cells was isolated by using RNeasy-Kit from Qiagen. cDNA was synthesized with the SMART Technology (Becton Dickenson). For the second strand PCR the following primers were used (Table III): (1) reverse constant IgM (con μ): 5'-GCC ACG CTG CTC GTA TCC GAC G-3' (SEQ ID NO:11); (2) reverse constant Kappa (con K): 5'-AGC AGG CAC ACA ACA GAG GCA GTT CC-3' (SEQ ID NO:12). The forward primers were included in the SMART-Kit. For sequencing the following primers have been used: (3) IgM sequence (μ seq.): 5c-GCT GCT CGT ATC CGA CGG-3' (SEQ ID NO:13), and (4) Kappa sequence (κ seq.): 5'-CAC AAC AGA GGC AGT TCC-3' (SEQ ID NO:14). Sequencing was performed at Microsynth AG (Balgach, Switzerland) and sequences were compared with existing germline sequences using the V-Base DNAplot software (http://www dot mrc-cpe dot cam dot ac dot uklDNAPLOT dot php?menu=901).

TABLE I

IATS Serotypes of P. aeruginosa resference strains

| IATS Serotype | Specification |
|---|---|
| O1 | PA53 (IT4) |
| O2 | E576 (IT3) |
| O3 | 6510 (Habs3) |
| O4 | 6511 (Habs4) |
| O6 | PA220 (IT1) |
| O7 | Fisher 6 (IT6) |
| O10 | Fisher 5 (IT5) |
| O11 | Fisher 2 (IT2) |
| O16 | Fisher 7 (IT7) |

TABLE II

Clinical isolates of P. aeruginosa serotype IATS O11

| # Isolate | Source of isolate |
|---|---|
| 2309.36 | urine |
| 2309.38 | ear |
| 2309.58 | blood |
| 2309.60 | urine |
| 2309.61 | urine |
| 2309.65 | tracheal secretion |
| 2310.49 | urine |
| 2310.55 | blood |
| 2311.58 | tracheal secretion |
| 2312.25 | tracheal secretion |
| V02 610 | gall bladder |
| VA 1014 | ear |
| VA 26939 | lung (BAL) |
| VA 28/1 | wound |
| VA 2813 | wound |
| VA 3348 | lung (BAL) |
| VA 3805 | eye |
| VA 4156/1 | wound |
| VA 695 | wound |
| VA 843 | tracheal secretion |
| FT-2 | Reference strain |

Whole Cell ELISA

Bacteria from different clinical isolates (see Table II) were grown in Luria broth medium at 37° C. to an optical density at 600 nm of 1, and fixed with 37% Formalin (final concentration of formalin: 0.5%) over night at 37° C. The fixed bacteria were diluted 1:50 in PBS and immobilized on ELISA plates. After blocking the plates with PBS containing 5% (v/v) fetal calf serum, the monoclonal antibody 1BO11 was incubated with the fixed bacteria for 2 hours at 37° C. Alternatively, isolates of other serotypes were grown as described above and incubated with the monoclonal antibody 1BO11 or, as positive controls, with monoclonal antibodies specific for the respective serotypes (FIG. 3b, serotype-specific positive control monoclonal antibodies collectively called "positive control"). After washing the plates 3× with PBS-T, bound antibodies were detected with horseradish peroxidase-conjugated goat anti-human IgM antibody (#074-1003; KPL; Kirkegaard & Perry Laboratories, Inc. Gaithersburg, Md.) diluted 1:2000 in PBS containing 5% (v/v) FCS. The plates were incubated for 1 hour at 37° C., and washed 3× with PBS-T. Antibody-binding was visualized by adding 100 μl/well OPD (0.4 mg/ml Orthophenyldiamin in 24 mM citric acid and 52 mM di-sodium hydrogen phosphate containing 0.0012% (V/V) $H_2O_2$ substrate solution. Color reaction was stopped after 2-3 min by the addition of 50 μl/well 1 M HCl. Optical density was read on a ELISA reader at 490 nm using Softmax Pro® software.

Opsonophagocytosis Assay

In order to determine the biological activity, the monoclonal antibody 1BO11 was tested for its opsonophagocytic activity. For this purpose, P. aeruginosa bacteria of the serotype IATS O11, according to table 1, were grown in TSBG (30 g/l Tryptic Soy Broth containing 1% (w/v) Glucose) medium overnight. After washing twice the bacteria with cold PBS, the bacterial pellet was re-suspended in 5 ml 0.1 M Bi-Carbonate buffer, pH8.0. 50 μl of 5-(and 6)-carboxyfluorescein, succinimidyl ester (5(6)-FAM, SE; Molecular Probes, Eugene, Oreg.; 10 mg/ml in Dimethylsulfoxid) were added, and incubated at 37° C. for 1 hour. Bacteria were fixed by the addition of 100 μl 37% Formaldehyde and incubation over night at 37° C. To remove the unconjugated dye, bacteria were washed 6 times by centrifugation re-suspension in 20 ml cold sterile PBS. The labeled bacteria were stored at 4° C. until use. For the assay, an aliquot of the bacteria was diluted to an optical density at 550 nm of 1, followed by a 1:50 dilution HBSS-BSA (Hanks balanced salt solution containing 0.1% BSA). 20 μl of the bacteria were mixed with 10 μl of different dilutions of hybridoma cell culture supernatant containing the monoclonal antibody 1BO11, or a non-specific monoclonal control antibody respectively (data not shown). After 30 min incubation at 37° C., 10 μl of baby rabbit serum (Charles River Laboratories, Germany) was added as a source of complement, and the probes were incubated for another 30 min at 37° C. 40 μl of differentiated HL-60 cells (the promyelocytic cell line HL-60 was differentiated into granulocytic cells by incubating the cells for 3 days in Is-coves Modified Dulbecco's Medium (IMDM; Sigma) supplemented with 10% (v/v) Fetal Calf Serum and 100 mM di-methyl-formamide.) were added to the opsonized bacteria to obtain a final concentration of $1.25 \times 10^6$ cells/ml. After incubating for 90 min at 37° C. on a shaker, the cells were harvested by transferring to 2 ml of cell wash buffer (PBS-containing 0.02% (v/v) azide; Becton Dickenson). After centrifugation for 5 min at 250×g, the cell pellet was re-suspended in 150 μl Cell wash buffer and analyzed by flow cytometry. Positive opsonphagocytotic activity was determined by analyzing the green fluorescence of the HL-60 cells in comparison with background staining. Background staining was determined by incubating fluorescein-conjugated bacteria in the presence of complement with HL-60 cells.

In Vivo Protection of P. aeruginosa Infected Mice

Murine Burn Wound Model

The in vivo protective capacity of 1BO11 was determined in the murine burn wound sepsis model. NMRI-Mice (18-20 g; Charles River Laboratories) received 0.16 to 10 μg (corresponding to approximately 0.4 to 0.006 mg/kg body weight) in a volume of 0.1 ml of the monoclonal antibody 1BO11 intravenously 4 hours prior to challenge. As control, 0.1 ml of unspecific antibody supernatant was injected. For challenge, groups of 10 female mice were anesthetized in an atmosphere of 3-chloro-1,1,2-trifluoroethyl-difluoromethyl-ether (Ethrane, Abbott Lab., Chicago, Ill.). The mice were subjected to a 10 second ethanol burn over a 2 $cm^2$ area of the back. $2 \times 10^7$ cfu/mouse of the challenge organisms (P. aeruginosa IATS O11; clinical isolate 2310.55, see table 2) suspended in 0.5 ml PBS were injected immediately subcutaneously into the burned area. The animals were observed for 7 days. As a measure of protection survival rate 3 days after challenge is shown.

Acute Lung Infection Model

To evaluate the protective capacity of 1BO11 against lung infection with P. aeruginosa, an acute lung infection model was used. 10 μg (0.4 mg/kg) 1BO11 was injected i.v. to BALB/c mice. Thereafter 40 μl of a $4.0 \times 10^7$/ml solution of strain 2310.55 (table 2) (corresponding to $1.6 \times 10^6$ per mouse) was applied intra-tracheally into the lower left bronchus using a curved bead-tipped needle under deep anesthesia. This dose was chosen as it led to limited mortality only. After 6, 12, 24 and 48 hours mice were sacrificed and lungs and spleens removed aseptically. Organs were suspended in 3 ml PBS and homogenised for 45 seconds with a blender on ice. Serially diluted organ homogenates (0.1 ml) were plated on modified Conradi Drigalski's agar to determine CFU/lung or CFU/spleen.

Determination of the Activation of the Classical Complement Pathway by Monoclonal Antibodies To determine eventual spontaneous triggering of the classical complement pathway by IgM-aggregates formed during downstream processing, 1BO11 antibody of a defined concentration was incubated in serum from a healthy donor for 30 minutes at 37° C. The reaction was then stopped in 10 mM EDTA, and the complement activation fragment C4d was detected by commercial ELISA (Quidel Corp, San Diego). As positive controls, IgM-antigen complexes consisting of 1BO11 antibody and its cognate LPS antigen were used.

EXAMPLES

Example 1

DNA and Amino Acid Sequences of 1BO11

The antibody specificity is determined by the DNA- and amino acid-sequence, respectively. DNA sequences of the variable fragments of the heavy and light chains were determined. Briefly, total RNA of the hybridoma cells was isolated, and reverse transcribed into complete cDNA using the SMART Technology (Becton Dickinson). By this approach, a universal primer was added at the 5' end of the cDNA. Using this primer and the Cκ and Cμ-specific primers depicted in Table III, the IgM and Kappa variable regions and part of the constant regions were amplified by PCR. The PCR fragments were then cleaned up by excision from agarose gels, and used as templates for sequencing with the primers depicted in Table III.

TABLE III

Primers used for PCR-amplification and sequencing of the variable regions of IgM heavy chains and Kappa light chains of 1BO11

| Primer | Sequence | | Application |
|---|---|---|---|
| Con μ | 5'-GCC ACG CTG CTC GTA TCC GAC G-3' | (SEQ ID NO: 11) | PCR |
| Con κ | 5'-AGC AGG CAC ACA ACA GAG GCA GTT CC-3' | (SEQ ID NO: 12) | PCR |
| μ seq. | 5'-GCT GCT CGT ATC CGA CGG-3' | (SEQ ID NO: 13) | Sequencing |
| κ seq. | 5'-CAC AAC AGA GGC AGT TCC-3' | (SEQ ID NO: 14) | Sequencing |

The sequences of the variable regions were subsequently compared with the Vbase Index. The results of the comparison with germline sequences are expressed as numbers of "replacement and silent" mutations (R:S), as depicted in Table IV. The DNA sequences and amino acid sequences are depicted in FIGS. 1 and 2.

TABLE IV

Ratio replacement vs. silent mutations from germline sequences

| | Heavy chain | | Light chain | |
|---|---|---|---|---|
| | Germline | R:S | Germline | R:S |
| 1BO11 | DP-53 | 17:3 | DPK-18 | 0:2 |

Example 2

Recognition of Clinical Isolates of *P. aeruginosa* Serotype IATS O11 by Monoclonal Antibody 1BO11

1BO11 has been generated by immunizing a healthy volunteer with an octavalent O-PS-Toxin A vaccine. The vaccine contains the IATS O11 reference strain FT-2. To investigate whether 1BO11 raised against the LPS of this strain also recognizes other isolates of the IATS O11 serotype, a wide range of clinical isolates from different hospitals was collected (see table 2). The serotype of all isolates was determined using a commercially available serotype agglutination kit. The serotypes were confirmed by PCR. Different clinical isolates of serotype IATS O11 (FIG. 3a) as well as other serotypes (FIG. 3b) were then tested for the binding to 1BI11 by whole cell ELISA.

1BO11 reacted strongly with all tested IATS O11 isolates, with the exception of two weak reactions which was due to low LPS expression on the surface of these isolates. Furthermore, binding was exclusively observed with isolates of IATS O11 serotype and no binding with various isolates of serotypes O1, O2, O3, O6 or O10 occurred. Integrity of these isolates was assured using other monoclonal antibodies against the respective serotype as positive controls.

Example 3

In Vitro Activity of 1BO11: Opsonophagocytic Activity

The in vitro biological activity of 1BO11 was assessed using a flow cytometry-based opsonophagocytosis assay. FITC-conjugated *P. aeruginosa* of serotype IATS O11 was incubated with serially 1BO11 in the presence of normal rabbit serum as a complement source.

Figure 4:
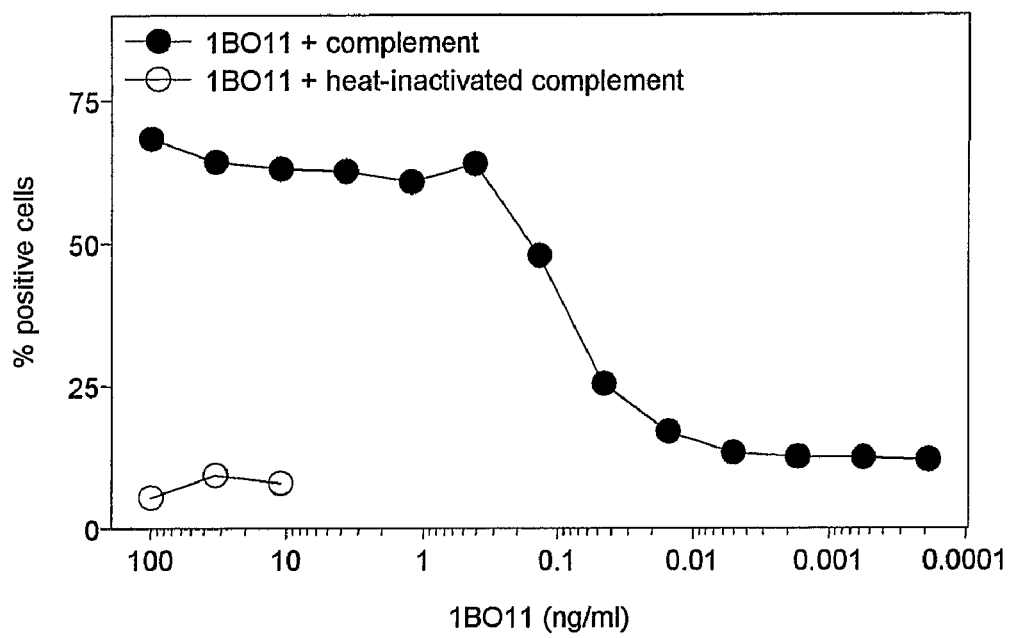
FIG. 4 relates to the opsonophagocytotic activity of the monoclonal antibody 1BO11 directed against *P. aeruginosa* serotype IATS O11.

The opsonized bacteria were incubated with differentiated HL-60 cells (a promyelotic cell line, ATCC: CCL-240; differentiation to monocytes was achieved by the addition of 0.1M di-methyl-formamide for 3 days). Opsonophagocytosis was analyzed by FACS. Positive opsonphagocytotic activity was determined by analyzing the green fluorescence of the HL-60 cells in comparison with background staining (FITC-conjugated bacteria with HL-60 cells in the absence of serum but in the presence of complement). The results are shown in FIG. 4.

1BO11 mediated phagocytosis of *P. aeruginosa* of IATS O11 serotype in a dose-dependent manner (filled circles). No phagocytosis was observed if heat-inactivated complement was used (empty circles). Opsonophagocytotic activity ($OA_{50}$) of 1BO11, defined as the concentration resulting in the half-maximal percentage of FITC-positive HL-60 cells, was 0.1 ng/ml. Activity at such a low dose indicates high effector potential of 1BO11.

Example 4

In Vivo Protective Capacity of the Monoclonal Antibody 1BO11

Figure 5:
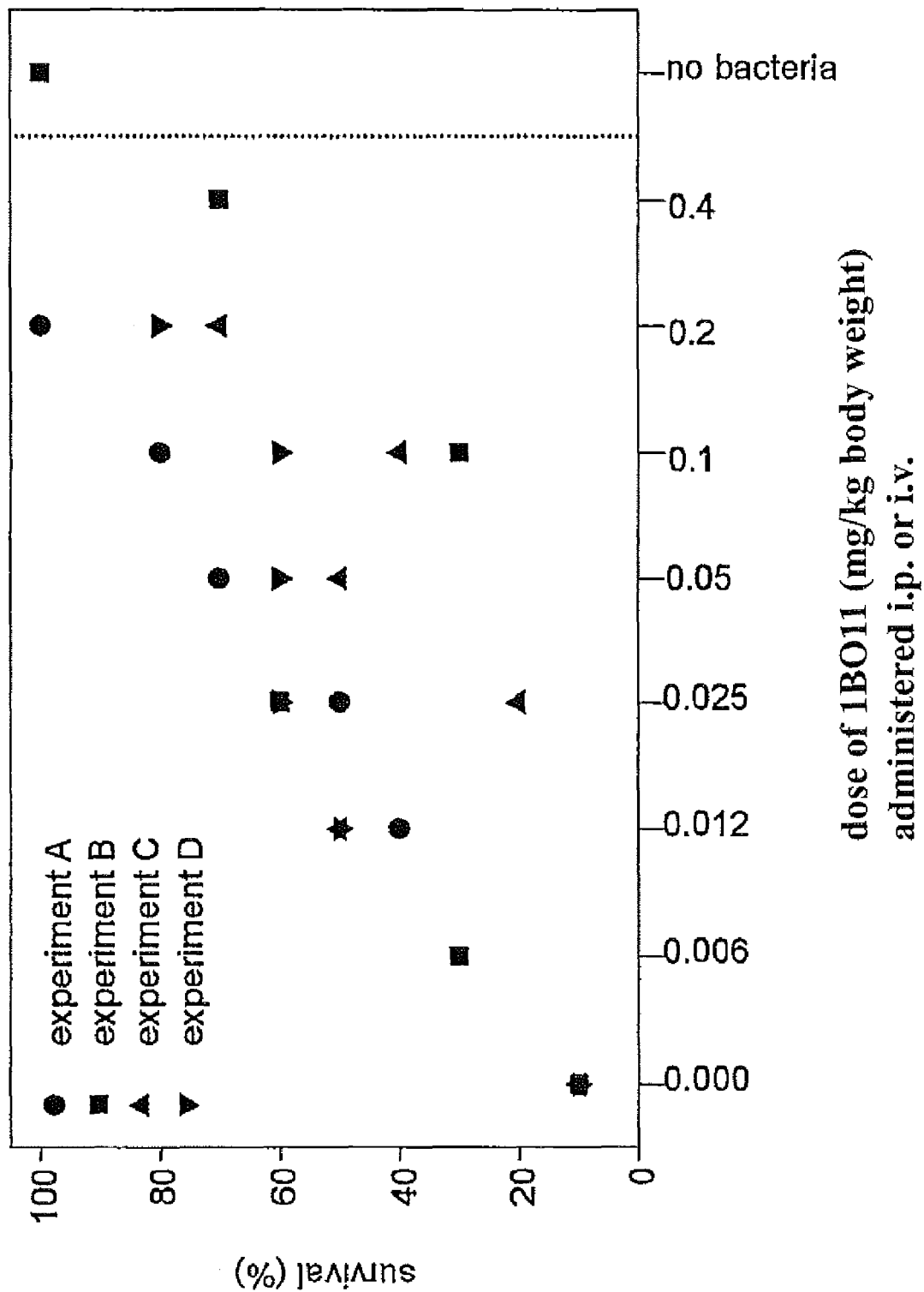
FIG. 5 relates to the pharmocodynamics of the monoclonal antibody 1BO11 in mice. The in vivo protective capacity of 1BO11 was assessed in a murine burn wound sepsis model. Different doses of 1BO11 were administered i.p. or i.v. to NMRI mice. Survival rates three days after challenge are shown.

In vivo protective capacity of 1BO11 was assessed in a murine burn wound sepsis model. Different doses of 1BO11 were administered i.p. or i.v. to NMRI mice. After three hours, a 2×2 cm burn wound was inflicted and $2\times10^7$ CFU *P. aeruginosa* strain 2310.55 (O11) were injected s.c. under the burned skin area. Mice received analgesics during the entire experimental period. Survival was monitored three times daily. Survival rates three days after challenge are shown in FIG. 5. Pooled data from 4 individual experiment (labelled A-D) are included.

Doses of >0.2 mg/kg body weight conferred 70-100% protection from systemic *Pseudomonas* challenge. Administration of decreasing doses resulted in lower survival rates. Death was a direct result of *Pseudomonas* infection since mice with burn wounds but no *Pseudomonas* infection had a 100%-survival rate. These data demonstrate the in vivo efficacy of 1BO11 against system infection with *P. aeruginosa*.

Example 5

Increased Bacterial Clearance from Lung and Spleen After Acute Respiratory Challenge To evaluate whether 1BO11 might be capable of clearing respiratory *Pseudomonas* infection a model of acute lung infection in mice was used. For this purpose, 1BO11 (0.4 mg/kg body weight) was administered i.v. prior to intratracheal lung challenge with *P. aeruginosa* strain 2310.55. The challenge-dose was chosen to result in minimal mortality only. Therefore clearance of bacteria from lung was chosen as evaluation parameter.

Figure 6:
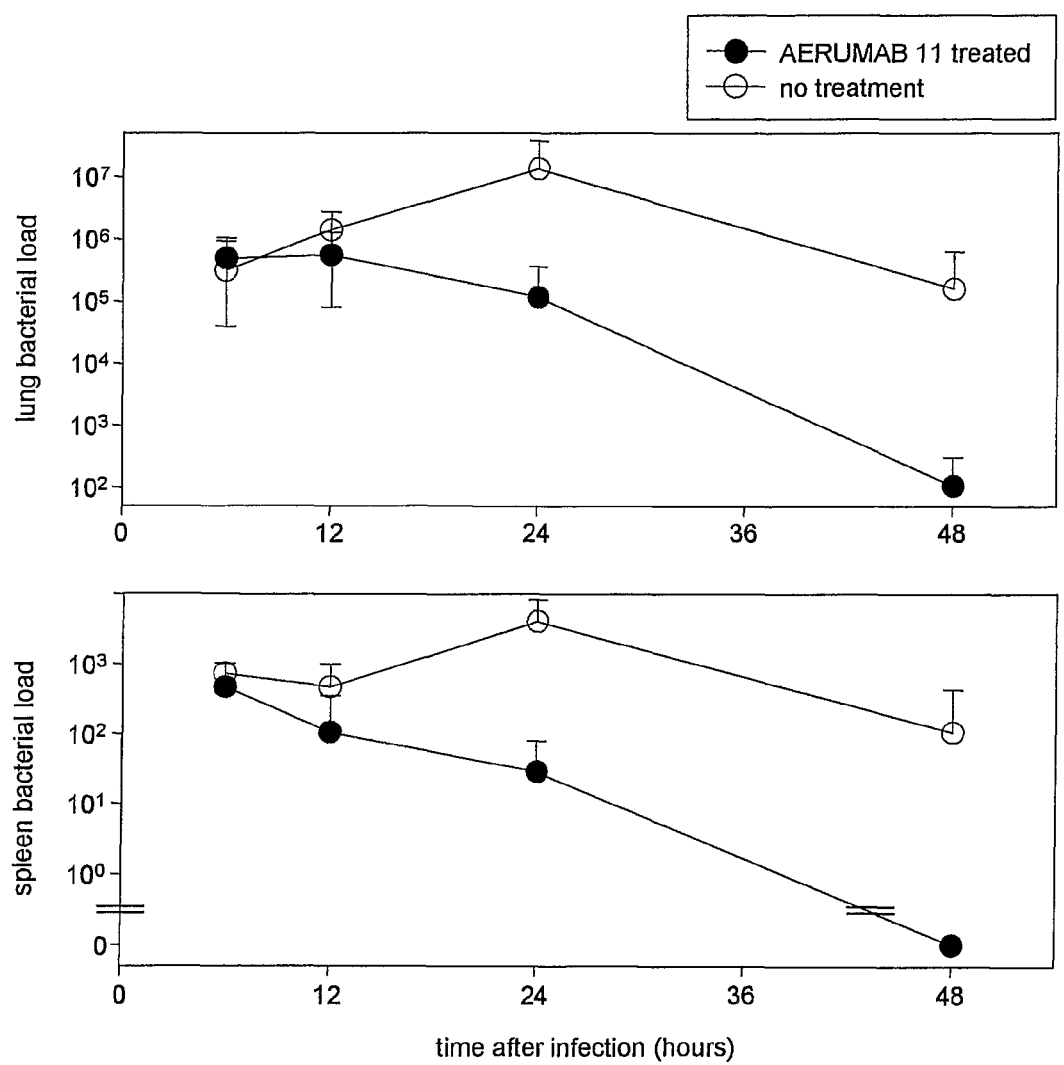
FIG. 6 relates to the pharmacodynamics of the monoclonal antibody 1BO11 in mice. The ability of 1BO11 to mediate clearance of *P. aeruginosa* from lung and spleen after lung infection was assessed in an acute lung infection model in mice. 1BO11 was administered i.v. prior to lung infection with *P. aeruginosa*. Bacterial load in lung and spleen was assessed 6, 12, 24 and 48 hours after infection.

Application of 1BO11 lead to rapid clearance of *P. aeruginosa* from the lung (FIG. 6). This finding is surprising as IgM antibodies do not normally penetrate into lung tissue. After 48 hours bacteria were completely cleared whereas at this time-point in non-treated animals infection was still ongoing. Similar to the course of *P. aeruginosa* pneumonia in humans, bacterial infection can become systemic, reflected in this experiment by appearance of *P. aeruginosa* in spleen. Complete resolution of systemic infection was mediated by 1BO11 while bacteria were still present in non-treated mice (FIG. 6). These findings indicate the potential of 1BO11 for treatment of respiratory *P. aeruginosa* infections, such as nosocomial pneumonia.

Example 6

Cross-Reactivity of the Monoclonal Antibody 1BO11 to Human Tissues

In order to exclude unwanted non-specific binding of 1BO11 to human tissues, 1BO11 was tested for cross-reactivity according to "FDA Points to Consider in the Manufacture and Testing of Monoclonal Antibody Products for Human Use (1997)" and "The Rules Governing Medicinal Products in the European Community Vol. 3a (1994). The tissues employed are listed in the following table. The tissues were each obtained from three unrelated donors to minimize the chances of donor specific factors affecting antibody binding.

TABLE V

Human tissues used for testing potential 1BO11 cross-reactivity

| Adrenal | Bladder | Blood cells | Blood vessels (Endothelium) |
|---|---|---|---|
| Bone marrow | Breast | Cerebellum | Cerebral cortex |
| Colon | Eye | Fallopian tube | Heart |
| Ileum (gastrointestinal tract) | Kidney (glomerulus, tubule) | Liver | Lung |
| Lymph node | Ovary | Pancreas | Parathyroid |
| Parotid | Peripheral nerve | Pituitary | Placenta |
| Prostate | Skin | Spinal cord | Spleen |
| Stomach | Striated muscle | Testis | Thymus* |
| Tyroid | Tonsil | Ureter | Uterus (cervix, endometrium) |

*Tissue from only one donor available for use.

No cross-reactivity to any of these tissues was observed (data not shown). Based on these results it seems likely that no non-specific binding to tissue will occur in vivo, thus resulting in limited inflammatory side-effects.

Example 7

Complement Activation by the Monoclonal Antibody 1BO11

Figure 7:
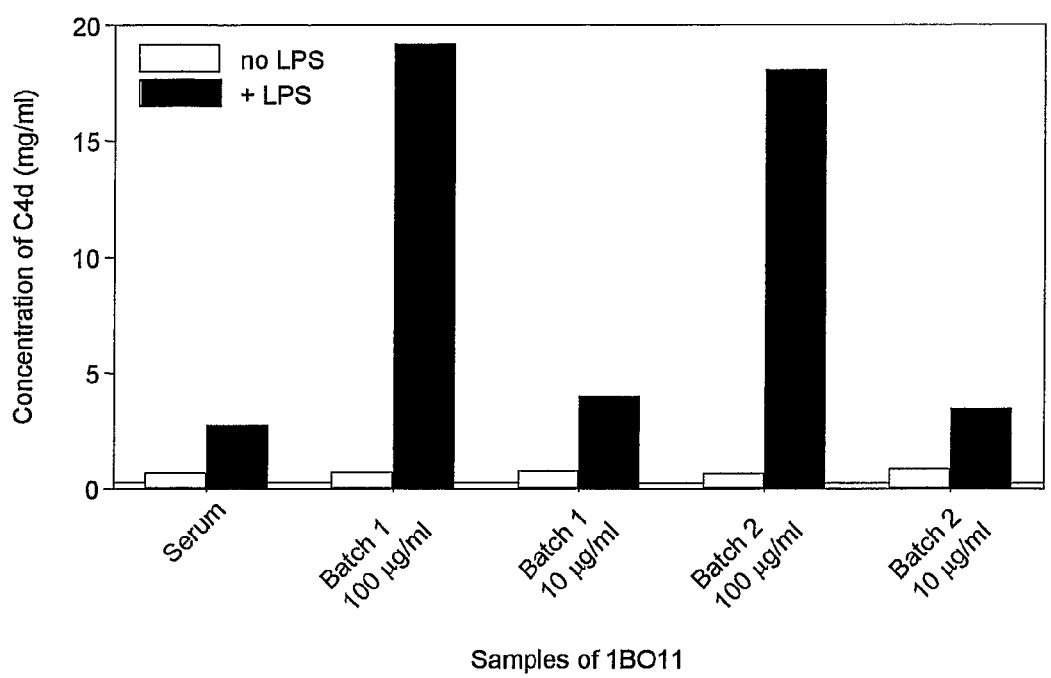
FIG. 7 relates to the complement activation of the monoclonal antibody 1BO11. The results of an in vitro assay measuring the generation of the complement component C4d upon mixing 1BO01 with human normal serum are shown. Generated C4d was detected by ELISA. Two batches of 1BO11 were tested at two different concentrations, 100 μg/ml and 10 μg/ml in serum. The serum alone control is indicated as 0 μg/ml.

Human antibodies administered in vivo may cause adverse reactions by the spontaneous activation of complement. Such an activation of the classical complement pathway can be tested by an in vitro assay measuring the generation of the complement component C4d upon mixing 1BO11 with human normal serum and detecting C4d by commercial ELISA (Quidel Corp., San Diego). Two batches of 1BO11 produced under GMP conditions (termed "Batch 1" and "Batch2") were tested at two different concentrations, 100 μg/ml and 10 μg/ml, in serum. The serum alone control is indicated as 0 μg/ml. The results are shown in FIG. 7.

There was no spontaneous generation of C4d triggered by 1BO11 in the serum (white bars), whereas high levels of C4d were generated in the presence of 10 μg/ml LPS of *P. aeruginosa* serotype IATS O11 (black bars). These results indicate that 1BO11 will show a minimal amount of spontaneous inflammatory side-effects when used in humans.

The invention claimed is:

1. A human monoclonal antibody specific for lipopolysaccharide (LPS) of the *P. aeruginosa* LPS serotype IATS 011 wherein the variable region of the light chain of the antibody has the amino acid sequence of SEQ ID NO:7 and the variable region of the heavy chain has the amino acid sequence of SEQ ID NO:8; or a variant of said antibody capable of binding said LPS wherein the amino acid sequence of the variable region of the light chain of the antibody is at least 85% homologous to SEQ ID NO:7 and the amino acid sequence of the variable region of the heavy chain of the antibody is at least 85% homologous to SEQ ID NO:8.

2. The human monoclonal antibody of claim 1, wherein the light chain is of the kappa type.

3. The human monoclonal antibody of claim 1, wherein the light chain is of the lambda type.

4. The human monoclonal antibody of claim 1, wherein the heavy chain is of the IgM, IgA or IgG type.

5. The human monoclonal antibody of claim 4, wherein the heavy chain is of the IgM type.

6. The human Monoclonal antibody of claim 1, wherein the antibody consists entirely of human amino acid sequence.

7. The human monoclonal antibody of claim 1, wherein the antibody exhibits essentially human antigen recognition.

8. The human monoclonal antibody of claim 1, wherein the antibody comprises a modification selected from the group consisting of oligomerization, conjugation to a drug, and conjugation to a label.

9. A hybridoma capable of producing the human monoclonal antibody of claim 1.

10. An isolated host cell capable of producing the human monoclonal antibody of claim 1.

11. A pharmaceutical composition comprising at least one human monoclonal antibody of claim 1 and optionally pharmaceutically acceptable ingredients.

12. A method of protecting a human patient from *P. aeruginosa* infection or treating a *P. aeruginosa* infection in a human patient, said method comprising administering the human monoclonal antibody of claim 1 to said human patient.

13. The method of claim 12 wherein the *P. aeruginosa* infection is a hospital-acquired infection.

14. A test kit for the diagnosis of a *P. aeruginosa* infection in a sample comprising at least one human monoclonal antibody of claim 1 and optionally further suitable ingredients for carrying out the diagnostic test.

* * * * *

SEQUENCE LISTING

<160> NUMBER OF SEQ ID NOS: 14

<210> SEQ ID NO 1
<211> LENGTH: 16
<212> TYPE: PRT
<213> ORGANISM: Homo sapiens

<400> SEQUENCE: 1

Arg Ser Ser Gln Ser Leu Val Tyr Ser Asp Gly Asn Thr Tyr Leu Asn
1               5                   10                  15

<210> SEQ ID NO 2
<211> LENGTH: 7
<212> TYPE: PRT
<213> ORGANISM: Homo sapiens

<400> SEQUENCE: 2

Lys Val Ser Asn Arg Asp Ser
1               5

<210> SEQ ID NO 3
<211> LENGTH: 9
<212> TYPE: PRT
<213> ORGANISM: Homo sapiens

<400> SEQUENCE: 3

Met Gln Gly Thr His Trp Pro Leu Thr
1               5

<210> SEQ ID NO 4
<211> LENGTH: 5
<212> TYPE: PRT
<213> ORGANISM: Homo sapiens

<400> SEQUENCE: 4

Pro Tyr Trp Met His
1               5

<210> SEQ ID NO 5
<211> LENGTH: 16
<212> TYPE: PRT
<213> ORGANISM: Homo sapiens

<400> SEQUENCE: 5

Arg Ile Asn Ser Asp Gly Ser Thr Tyr Tyr Ala Asp Ser Val Lys Gly
1               5                   10                  15

<210> SEQ ID NO 6
<211> LENGTH: 8
<212> TYPE: PRT
<213> ORGANISM: Homo sapiens

<400> SEQUENCE: 6

Asp Arg Tyr Tyr Gly Pro Glu Met
1               5

<210> SEQ ID NO 7
<211> LENGTH: 112
<212> TYPE: PRT
<213> ORGANISM: Homo sapiens

<400> SEQUENCE: 7

Asp Val Val Met Thr Gln Ser Pro Leu Ser Leu Pro Val Thr Leu Gly
1               5                   10                  15

```
Gln Pro Ala Ser Ile Ser Cys Arg Ser Ser Gln Ser Leu Val Tyr Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gly Gly Thr Lys Val Glu Ile Lys
                100                 105                 110
```

<210> SEQ ID NO 8
<211> LENGTH: 116
<212> TYPE: PRT
<213> ORGANISM: Homo sapiens

<400> SEQUENCE: 8

```
Glu Glu Gln Val Val Glu Ser Gly Gly Gly Phe Val Gln Pro Gly Gly
1               5                   10                  15

Ser Leu Arg Leu Ser Cys Ala Ala Ser Gly Phe Thr Phe Ser Pro Tyr
                20                  25                  30

Trp Met His Trp Val Arg Gln Ala Pro Gly Lys Gly Leu Val Trp Val
            35                  40                  45

Ser Arg Ile Asn Ser Asp Gly Ser Thr Tyr Tyr Ala Asp Ser Val Lys
    50                  55                  60

Gly Arg Phe Thr Ile Ser Arg Asp Asn Ala Arg Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Tyr Tyr Gly Pro Glu Met Trp Gly Gln Gly Thr Met Val
                100                 105                 110

Thr Val Ser Ser
        115
```

<210> SEQ ID NO 9
<211> LENGTH: 336
<212> TYPE: DNA
<213> ORGANISM: Homo sapiens

<400> SEQUENCE: 9

```
gatgttgtga tgactcagtc tccgctctcc ctgcccgtca cccttggaca gccggcctcc      60
atctcctgca ggtctagtca aagcctcgta tatagtgatg aaacacccta cttgaattgg     120
tttcagcaga ggccaggcca atctccaagg cgcctaattt ataaggtttc taaccgggac     180
tctggggtcc cagacagatt cagcggcagt gggtcaggca ctgatttcac actgaaaatc     240
agcagggtgg aggctgagga tgttggggtt tattactgca tgcaaggtac acactggcct     300
ctcactttcg gcggagggac caaggtggag atcaaa                              336
```

<210> SEQ ID NO 10
<211> LENGTH: 348
<212> TYPE: DNA
<213> ORGANISM: Homo sapiens

<400> SEQUENCE: 10

```
gaggagcagg tggtggagtc cggggggaggc tttgttcagc ctggggggtc cctgagactc      60
```

```
tcctgtgcag cctctggatt cacctttagt ccatactgga tgcactgggt ccgccaagct    120
ccagggaagg ggctggtgtg ggtctcacgt attaatagtg atgggagcac atactacgcg    180
gactccgtga agggccgatt caccatctcc agagacaacg ccaggaacac actgtatctg    240
caaatgaaca gtctgagagc cgaggacacg gctgtgtatt actgtgcaag agatcgatac    300
tatggccccg aaatgtgggg ccaagggaca atggtcaccg tctcttca                 348

<210> SEQ ID NO 11
<211> LENGTH: 22
<212> TYPE: DNA
<213> ORGANISM: Artificial
<220> FEATURE:
<223> OTHER INFORMATION: Chemically synthesized

<400> SEQUENCE: 11
gccacgctgc tcgtatccga cg                                              22

<210> SEQ ID NO 12
<211> LENGTH: 26
<212> TYPE: DNA
<213> ORGANISM: Artificial
<220> FEATURE:
<223> OTHER INFORMATION: Chemically synthesized

<400> SEQUENCE: 12
agcaggcaca caacagaggc agttcc                                          26

<210> SEQ ID NO 13
<211> LENGTH: 18
<212> TYPE: DNA
<213> ORGANISM: Artificial
<220> FEATURE:
<223> OTHER INFORMATION: Chemically synthesized

<400> SEQUENCE: 13
gctgctcgta tccgacgg                                                   18

<210> SEQ ID NO 14
<211> LENGTH: 18
<212> TYPE: DNA
<213> ORGANISM: Artificial
<220> FEATURE:
<223> OTHER INFORMATION: Chemically synthesized

<400> SEQUENCE: 14
cacaacagag gcagttcc                                                   18
```